(12) United States Patent
Grafton et al.

(10) Patent No.: US 7,892,256 B2
(45) Date of Patent: Feb. 22, 2011

(54) HIGH STRENGTH SUTURE TAPE

(75) Inventors: R. Donald Grafton, Naples, FL (US); Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 352 days.

(21) Appl. No.: 10/970,380

(22) Filed: Oct. 22, 2004

(65) Prior Publication Data

US 2005/0192631 A1  Sep. 1, 2005

Related U.S. Application Data

(63) Continuation-in-part of application No. 10/358,399, filed on Feb. 5, 2003, now Pat. No. 6,994,719, which is a continuation-in-part of application No. 10/160,176, filed on Jun. 4, 2002, now Pat. No. 7,029,490, which is a continuation-in-part of application No. 09/950,598, filed on Sep. 13, 2001, now Pat. No. 6,716,234.

(60) Provisional application No. 60/354,499, filed on Feb. 8, 2002, provisional application No. 60/350,040, filed on Jan. 23, 2002, provisional application No. 60/330,913, filed on Nov. 2, 2001, provisional application No. 60/512,861, filed on Oct. 22, 2003.

(51) Int. Cl.
*A61B 17/04* (2006.01)
*A61B 17/06* (2006.01)

(52) U.S. Cl. .......................... 606/228; 606/231; 600/37

(58) Field of Classification Search ................. 606/143, 606/228–232; 623/13.11; 600/37; 87/6; 132/321
See application file for complete search history.

(56) References Cited

U.S. PATENT DOCUMENTS

| | | | | |
|---|---|---|---|---|
| 3,971,202 A | * | 7/1976 | Windley | 57/205 |
| 4,946,467 A | * | 8/1990 | Ohi et al. | 606/228 |
| 5,180,636 A | * | 1/1993 | Harazoe et al. | 428/373 |
| 5,318,575 A | * | 6/1994 | Chesterfield et al. | 606/151 |
| 5,645,568 A | * | 7/1997 | Chervitz et al. | 606/228 |
| 5,741,451 A | * | 4/1998 | Dunbar et al. | 264/103 |

(Continued)

FOREIGN PATENT DOCUMENTS

EP  1 293 218 A1  3/2003

(Continued)

*Primary Examiner*—Todd E Manahan
*Assistant Examiner*—Amy Lang
(74) *Attorney, Agent, or Firm*—Dickstein Shapiro LLP

(57) ABSTRACT

A suture tape construct is made of braided high strength surgical suture material. A length of round braided suture extends along the entire length of the suture tape. A middle portion of the suture tape features a flat braid added to the round braided suture. The suture is incorporated centrally into the flat braid, providing a backbone to the construct. Transition sections at either end of the flat braid are tapered to allow the suture tape to pass easily through openings during surgical procedures. The suture tape is a braided construction of ultra-high molecular weight polyethylene fiber blended with fibers of one or more long chain synthetic polymers, preferably polyester. The suture tape is indicated for high demand orthopedic repairs such as arthroscopic reconstruction for acromioclavicular joint separation, for example. The broad footprint of the suture tape is appropriate for repairs in degenerative cuff tissue where tissue pull-through may be a concern.

18 Claims, 3 Drawing Sheets

U.S. PATENT DOCUMENTS

| | | | |
|---|---|---|---|
| 6,716,234 B2 * | 4/2004 | Grafton et al. | 606/228 |
| 2002/0029066 A1 * | 3/2002 | Foerster | 606/228 |
| 2004/0098049 A1 * | 5/2004 | Im et al. | 606/230 |
| 2005/0277985 A1 * | 12/2005 | Wert et al. | 606/228 |
| 2006/0155328 A1 * | 7/2006 | Foerster | 606/228 |

FOREIGN PATENT DOCUMENTS

| | | |
|---|---|---|
| EP | 0 561 108 A2 | 9/2003 |

* cited by examiner

HIGH STRENGTH SUTURE TAPE

This application is a continuation-in-part of U.S. application Ser. No. 10/358,399, filed Feb. 5, 2003, now U.S. Pat. No. 6,994,719 which is a continuation-in-part of U.S. application Ser. No. 10/160,176, filed Jun. 4, 2002, now U.S. Pat. No. 7,029,490 which claims the benefit of U.S. Provisional Application No. 60/354,499, filed Feb. 8, 2002, U.S. Provisional Application No. 60/350,040, filed Jan. 23, 2002 and U.S. Provisional Application No. 60/330,913, filed Nov. 2, 2001, which is a continuation-in-part of U.S. application Ser. No. 09/950,598, filed Sep. 13, 2001, now U.S. Pat. No. 6,716,234. This application claims the benefit of U.S. Provisional Application No. 60/512,861, filed Oct. 22, 2003.

BACKGROUND OF THE INVENTION

1. Field of the Invention

The present invention relates to high strength surgical suture materials and, more particularly, to suture tape constructs braided from blends of ultrahigh molecular weight polyethylene.

2. Brief Description of Related Art

Suture strength is an important consideration in any surgical suture material. Suture made from blends of ultrahigh molecular weight polyethylene (UHMWPE), have been developed, as disclosed in the related patent documents noted above and incorporated herein by reference. A surgical tape constructed of similar material would have improved utility for many surgical applications.

SUMMARY OF THE INVENTION

The present invention advantageously provides suture tape constructs made of high strength surgical suture material. In the broadest sense, the suture tape comprises a length of suture supporting a tape section of material having a flattened profile and a width greater than a thickness of the length of suture. Preferably the length of suture extends continuously through and beyond either end of the tape section.

The length of suture and the tape material are readily provided as textiles, but the suture tape construct could also be obtained from strip or sheet materials, for example. The term textile is intended to include all fiber materials, interlaced and non-interlaced, whether made by weaving, knitting, bonding, laminating, felting, or other processes. It can also refer to paper-like materials. All or some of the textile components can be bioabsorbable or resorbable, as known in the art.

The length of suture is most readily provided as a cord, preferably braided from suture material strands including UHMWPE fibers blended with fibers of one or more long chain synthetic polymers, most preferably polyester. The UHMWPE fibers impart strength, while the blended fibers, particularly polyester, improve tie down properties.

The tape section is easily provided as a flat braid added to the length of suture. According to an exemplary embodiment, the flat braid is formed around the length of suture. The flat braid is supported along a central portion of the length of suture. Transition sections are developed at either end of the flat braided tape section, which is shorter than the length of suture. The transition sections are tapered to allow the suture tape to pass easily through openings during surgical procedures. This and other features of the suture tape construct are described in further detail below.

The suture tape construct preferably is provided in discrete lengths. In an exemplary embodiment, a discrete 54" length of hollow round braided suture extends along the entire length of the suture tape construct. A central portion of the exemplary suture tape construct features a flat-braid tape section added to the round-braided length of suture. The ends of the flat braided tape section taper down to and are inserted into the length of suture. The round braided suture preferably is incorporated centrally into the flat braid, providing a backbone to the construct. The round braided length of suture extends 8" from either end of the flat-braided tape section.

In a preferred embodiment, the round braided length of suture includes a hollow braided multifilament cover formed of UHMWPE fiber braided with polyester and nylon fibers. The hollow braided cover optionally surrounds a fiber core made substantially or entirely of UHMWPE. The core preferably comprises three strands of UHMWPE, twisted at about 3 to 6 twists per inch. The cover preferably comprises 8 strands of UHMWPE braided with 6 strands of polyester. Colored strands of nylon can be incorporated as well. The tape section preferably is a flat braid of the same blend of UHMWPE and polyester as the cover.

UHMWPE fibers suitable for use in the present invention are marketed under the Dyneema trademark by Toyo Boseki Kabushiki Kaisha, and are produced in the U.S. by Honeywell under the trademark Spectra.

The suture tape of the present invention is ideal for most orthopedic procedures such as rotator cuff repair, achilles tendon repair, patellar tendon repair, ACL/PCL reconstruction, hip and shoulder reconstruction procedures, and replacement for suture used in or with suture anchors.

Handling properties of the high strength suture can be enhanced using various materials to coat the suture. The suture tape can be coated with wax (beeswax, petroleum wax, polyethylene wax, or others), silicone (Dow Corning silicone fluid 202A or others), silicone rubbers (NuSil Med 2245, NuSil Med 2174 with a bonding catalyst, or others), PTFE (Teflon, Hostaflon, or others), PBA (polybutylate acid), ethyl cellulose (Filodel) or other coatings, to improve lubricity of the braid, knot security, or abrasion resistance, for example.

Strands of a contrasting color can be added to the braided threads, for example, to enhance visibility, or the coloring of the round braided suture can contrast with that of the flat braid. Colored strands preferably are produced from dyed fibers of polyester or nylon. Other methods of differentiating between suture tapes or distinguishing opposite ends of a single suture tape also can be used, such as varying surface texture, coloring, or other visual cues.

Other features and advantages of the present invention will become apparent from the following description of the invention which refers to the accompanying drawings.

DETAILED DESCRIPTION OF THE INVENTION

Figure 1:
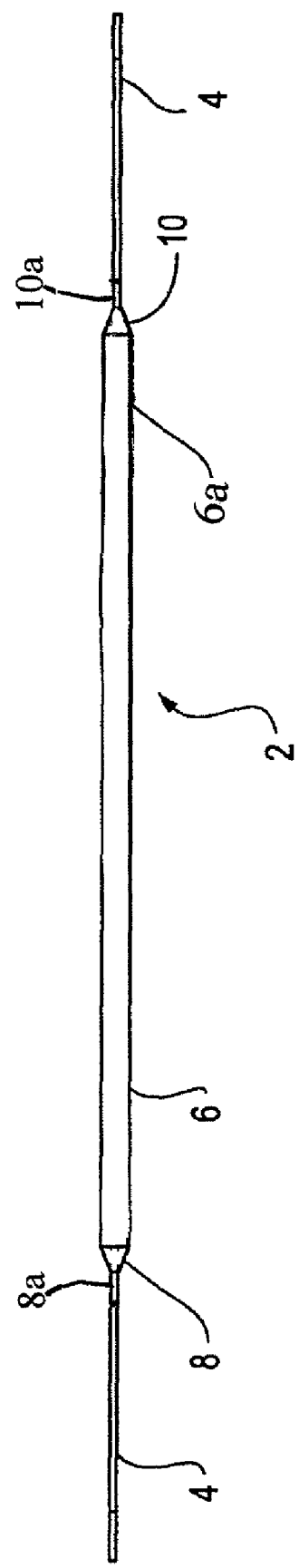
FIG. 1 illustrates a length of suture tape according to a preferred embodiment of the present invention.

Referring to FIG. 1, a length of suture tape 2 is illustrated. Suture tape 2 includes a length of round braided suture 4 (preferably Arthrex FiberWire™, sold by Arthrex, Inc. of Naples, Fla. and having the structure disclosed in U.S. Pat. No. 6,716,234) extending along the length of the suture tape 2 construct. The width of the suture tape 2 expands centrally by way of a flat braid 6 having a flattened profile 6a. The flat braid 6 incorporates suture 4 as a backbone of the construct.

Transitions 8, 10 at either end of the flat braid 6 taper down in the direction of the ends of the suture tape to #2 size high strength suture. Each transition (splice) is stitched, although other attachment methods, such as gluing, could be used. Preferably, the end 8a, 10a (FIG. 1) of flat braid 6 is accommodated inside (inserted into) the round braided suture 4 to provide a smooth junction. When making 2 mm tape, for example, the make up (warp fiber) uses five warps, with the option of using seven warps. One of the warps is US2 braid (with nylon inserts, described below). The other four warps are made from twist.

The US2 braid is made on a conventual's braiding machine using the same or similar specifications used for making Fiberwire™ and other loop suture products available from Arthrex, Inc. of Naples, Fla., with the additional introduction of the nylon insert. The distance is smaller and more frequent than that used for making of the loops. The nylon insert is put in the braid to enable performing the splice.

The braiding of the tape of the present invention is made in one process, using a flat braiding machine. On completion of a braided run, the braid is then transferred to a skein, and is dyed in the package using a D&C No. 6 Blue dye. On completion of this process, the skein is wound back to a bobbin and is then coated.

Each suture tape has a US2 suture at each end. The tape and suture is a complete structure, with a continuous strand of the suture running all the way through the tape. Preferably, there are no joins or glue used in each length. The suture transition to tape is tapered by removing the US2 braided warp from the inside of the tape, and at the same time taking out the nylon insert. Where the nylon has been taken out, it is replaced with a splicing needle. The remainder of the tape can now be spliced into the US2 braid, and any excess tape is cut off and hidden within the taper. The taper transition has characteristics similar to a finger trap: the harder it is pulled the tighter it becomes. Each length falls in line with a specified tolerance. Opposing tips 12, 14 of the suture are stiffened with Loctite 4014, a product of Henkels, Düsseldorf, Germany. The entire suture tape construct is coated with a silicone elastomer. US2 suture on which the suture tape is based exhibits knot strength with an average peak load of about 13.50 kg force. ASTM D2256 describes industry standard testing methods to determine the breaking load, elongation, single strand strength, knot breaking strength, loop breaking strength, tenacity and breaking tenacity of monofilaments, multi filaments and spun yarns.

The suture tape is provided in overall lengths of six to eight feet, preferably finished to 54 inches. Central tape portion 6 is about 3-4 feet in length, preferably 38 inches. The suture ends of the suture tape each are about one foot in length, preferably finished to 8 inch lengths. The suture tape is provided in 2.25 mm and 4.0 mm widths.

The suture tape material is a braided construction of polyester and long chain polyethylene (UHMWPE), produced by Pearsalls Limited, Taunton, England. Suture tape 2 preferably is coated, on both the suture and the tape, with a silicone elastomer. An exemplary elastomer product is MED-2174 by NuSil Technology, Carpinteria, Calif.

The suture tape construct is indicated for high demand orthopedic repairs such as arthroscopic reconstruction for acromioclavicular joint separation, for example. The broad footprint of the suture tape is appropriate for repairs in degenerative cuff tissue where tissue pull-through may be a concern. In general, the suture tape construct is used to capture tissue, such as tendon or bone, and secure the tissue in an anatomical position by attachment of the suture tape construct. Attachment is often achieved by tying the suture tape construct to itself around another tissue to complete the reattachment.

Referring next to FIGS. 2-5, a surgical repair will be described in which suture tape constructs according to the present invention are utilized. This example relates to treatment of acromioclavicular (AC) joint separation, although the invention is not so limited. AC joint separation is one of the most common shoulder injuries, yet its treatment has remained largely non-operative due to the unreliable and invasive nature of current surgical procedures. Arthroscopic AC joint reconstruction was not an option due to the lack of reliable instrumentation, strong and resilient implants, and reproducible techniques.

The invention provides methods and apparatus that offer a reproducible, minimally invasive technique of anatomic reconstruction of the coracoclavicular ligaments that will not compromise coracoid or clavicular bone, with rapid rehabilitation and return to normal activities. The suture tape constructs can be used for operational treatment of acute AC joint separations (Rockwood type III through VI), in active patients unwilling to accept disformity, dysfunction, or pain in the affected shoulder girdle. Chronic AC separations that are painful and result in a dysfunctional shoulder girdle with significant deformity also can be treated.

Figure 2:
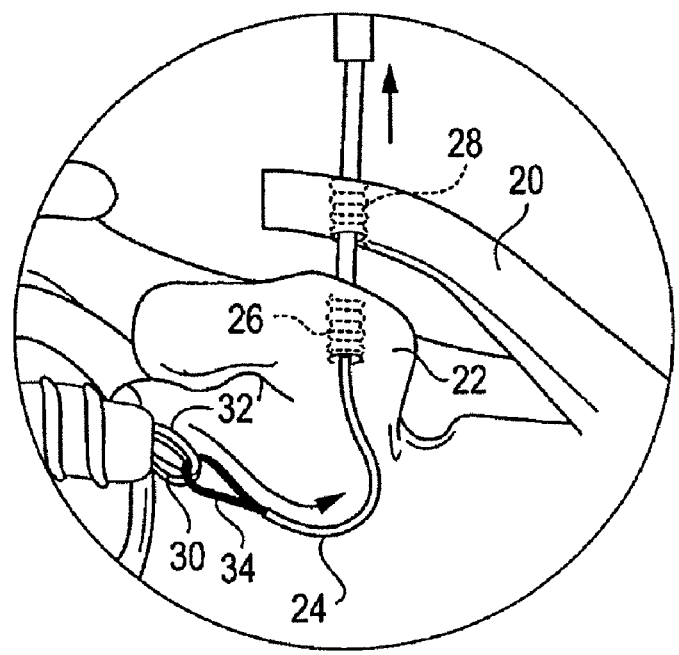
FIG. 2 illustrates an operative step in repairing in a shoulder repair procedure using the suture tape of FIG. 1.
Figure 3:
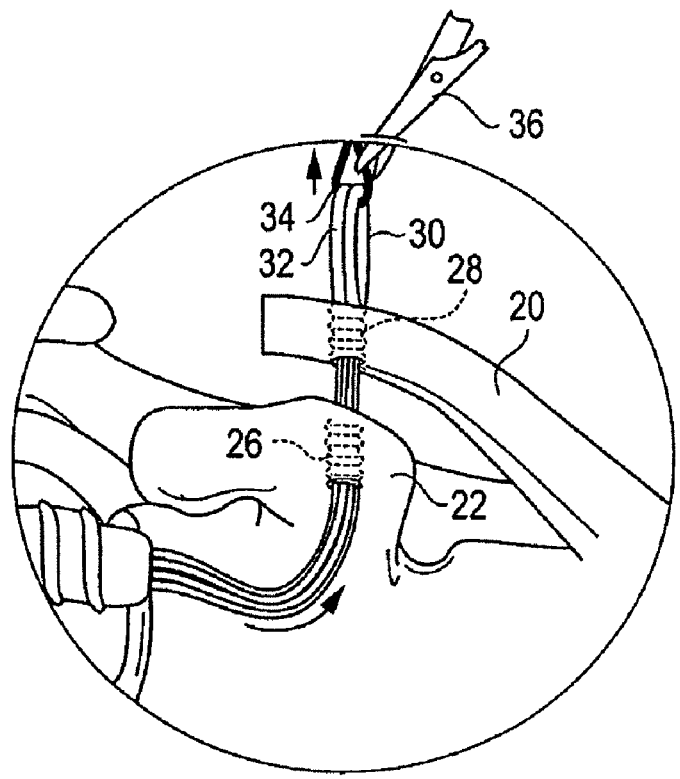
FIG. 3 illustrates an additional operative step in repairing in a shoulder repair procedure using the suture tape of FIG. 1.

FIG. 2 illustrates a shoulder joint in which the distal clavicle 20 has been resected to insure complete reduction and to avoid the potential of subsequent AC joint arthritis. In chronic AC separations, it may be necessary to carry out the arthroscopic dissection medially under the clavicle to resect the scarred and/or calcified scar tissue between the coracoid 22 and the clavicle 20. The surgeon may perform an open distal clavicle resection, since a small incision over the distal clavicle 20 will be necessary later in the procedure to drill through and tie sutures over the distal clavicle 20.

A 2.4 mm drill tipped guide pin (not shown) is drilled through the clavicle 20 and the base of the coracoid 22. A 4.5 mm cannulated drill (not shown) is used over the guide pin to create a tunnel through the clavicle 20 and the base of the coracoid 22, and the 2.4 mm guide pin is removed, leaving the 4.5 mm drill in place. A nitinol suture passing wire 24 is inserted into the cannulation of the drill, loop first from the clavicle 20 side, and is advanced until the loop exits the drill at the base of the coracoid 22. The nitinol suture passing wire 24 is retrieved with a grasper and pulled out of an anterior working portal 26. The 4.5 mm drill is removed and the suture passing wire 24 is left in place.

A coracoid screw 26 is inserted over the nitinol suture passing wire 24 with a driver (not shown) through the clavicle 20 and into the coracoid 22. The coracoid screw 26 is advanced until its distal thread extends just beyond the cortex at the base of the coracoid 22.

A headed clavicle screw 28 is then inserted over the nitinol suture passing wire 24 with the driver into the clavicle 20 and advanced until the threads are all within the clavicle 20 and the head of the clavicle screw 28 is proud on the superior clavicular cortex.

Two 2 mm suture tape strands 30, 32 are inserted into the loop 34 of the nitinol suture passing wire 24. Tape strands 30, 32 are pulled halfway through loop 34 to obtain a four-strand configuration. The suture tape strands 30, 32 are pulled through the coracoid screw 26 and the clavicular screw 28 so that the two doubled-over center portions of suture tape strands 30, 32 exit the top of the clavicle 20. The loop 34 is severed with cutters 36 to release the suture tape strands 30, 32.

Figure 4:
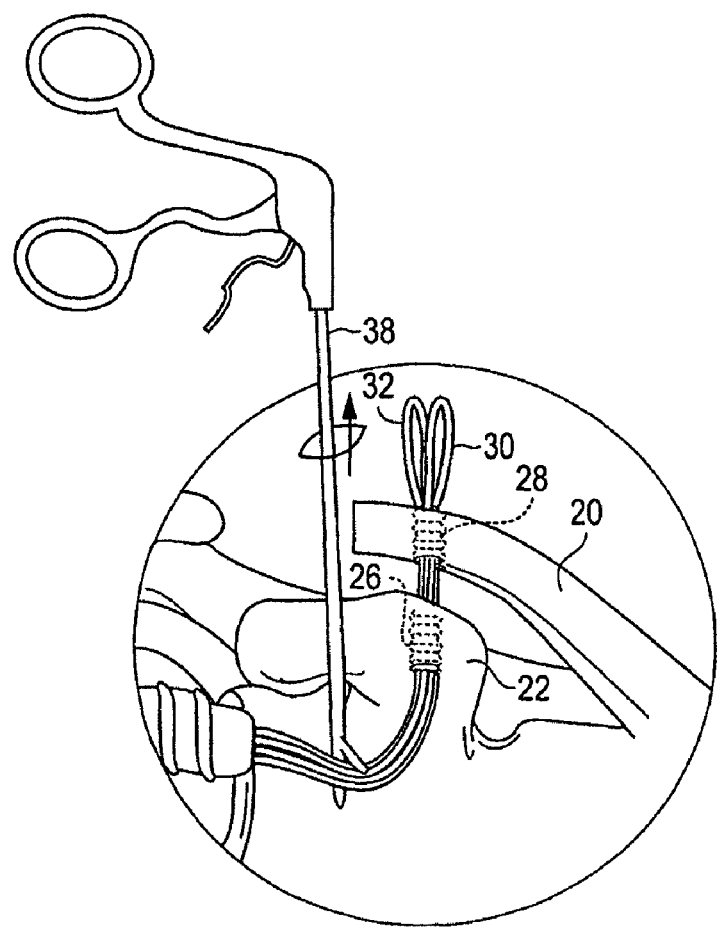
FIG. 4 illustrates a further operative step in repairing in a shoulder repair procedure using the suture tape of FIG. 1.
Figure 5:
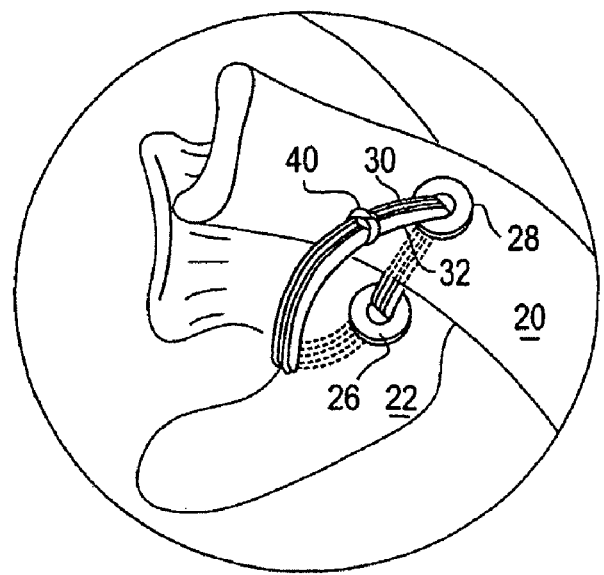
FIG. 5 illustrates a completed shoulder repair procedure using the suture tape of FIG. 1.

Referring to FIG. 4, four free ends of tape strands 30, 32 remain extending outside the anterior working portal. A suture retriever 38 is used anterior to and at the distal end of the clavicle 20 to draw the free ends of the suture tape strands 30, 32 through the anterior portal and into the joint space. The free ends are pulled out of the existing incision up over the anterior border and over the distal end of the clavicle, as indicated by the arrow in FIG. 4. With traction released, pressure is applied to the clavicle 20 by an assistant as the 2 mm suture tape strands 30, 32 are tied over anterior and/or lateral borders of the clavicle 20 with a racking hitch 40.

After screw and suture placement the region between the undersurface of the clavicle 20 and top of the coracoid 22 should be rasped to provide a bleeding bone bed, and packed with morselized cancellous bone from the distal clavicle resection. This will provide the necessary biological component to stimulate fibrosis of the clavicle 20 to the coracoid 22 for long term support of the reconstructed AC joint.

Although the present invention has been described in connection with preferred embodiments, many modifications and variations will become apparent to those skilled in the art.

What is claimed as new and desired to be protected by Letters Patent of the United States is:

1. A surgical suture comprising:
    a length of round, high strength suture having a thickness;
    a tape section having a flattened profile and being provided as a flat braid formed of braided strands, the flat braid being formed around the length of the round suture, the flat braid being supported on the length of the round suture and having a width greater than the thickness of the round suture, the length of round, high strength suture passing through an entire length of the flat braid; and
    a transition provided at each opposite end of the tape section, the transition being stitched or glued so that the width of the tape section tapers down to the thickness of the suture, each transition joining the tape to the length of the round, high strength suture passing therethrough, so that each opposite end of the tape section is inserted into the length of round, high strength suture.

2. A surgical suture as in claim 1, wherein the length of suture is continuous.

3. A surgical suture as in claim 1, wherein the length of suture is longer than the tape section.

4. A surgical suture as in claim 1, wherein the length of suture is a textile material.

5. A surgical suture as in claim 4, wherein the length of suture includes braided strands.

6. A surgical suture as in claim 5, wherein the length of suture includes a hollow braided cover.

7. A surgical suture as in claim 6, wherein the hollow braided cover includes ultrahigh molecular weight polyethylene fiber.

8. A surgical suture as in claim 6, wherein the hollow braided cover includes a blend of ultrahigh molecular weight polyethylene fibers and polyester fibers.

9. A surgical suture as in claim 6, further including a textile core.

10. A surgical suture as in claim 9, wherein the textile core includes twisted strands.

11. A surgical suture as in claim 10, wherein the twisted strands include ultrahigh molecular weight polyethylene fibers.

12. A surgical suture as in claim 1, wherein the tape section includes a textile material.

13. A surgical material as in claim 1, wherein the tape section includes ultrahigh molecular weight polyethylene.

14. A method of surgical repair comprising:
    capturing tissue with a suture tape construct, the suture tape construct comprising a length of round, high strength suture having a thickness, and a tape section having a flattened profile and being provided as a flat braid formed of braided strands, the flat braid being formed around the length of the round, high strength suture, the flat braid being supported on the length of suture material and having a width greater than the thickness of the round suture, the length of round, high strength suture passing through an entire length of the flat braid, and a transition provided at each opposite end of the tape section, the transition being stitched or glued so that the width of the tape section tapers down to the thickness of the suture, each transition joining the tape to the length of the round, high strength suture passing therethrough, so that each opposite end of the tape section is inserted into the length of round, high strength suture; and
    securing the tissue in an anatomical position by attachment of the suture tape construct.

15. A method as in claim 14, wherein the tissue is bone, and the suture tape construct is attached to other bone.

16. A method as in claim 14, wherein the step of capturing the tissue comprises passing through the tissue the suture tape construct.

17. A method as in claim 16, wherein the length of suture comprises a braided blend of ultrahigh molecular weight polyethylene and polyester.

18. A surgical reconstruction comprising:
    a suture tape construct comprising a length of suture having a thickness, and a tape section having a flattened profile and being provided as a flat braid formed of braided strands, the flat braid being formed around the length of the round, high strength suture, the flat braid being supported on the length of the round suture and having a width greater than the thickness of the round suture, the length of round, high strength suture passing through an entire length of the flat braid, and a transition provided at each opposite end of the tape section, the transition being stitched or glued so that the width of the tape section tapers down to the thickness of the suture, each transition joining the tape to the length of suture passing therethrough, so that each opposite end of the tape section is inserted into the length of round, high strength suture;
    wherein the suture tape construct is configured to capture tissue and secure it in an anatomical position.

* * * * *